(12) United States Patent
Chu et al.

(10) Patent No.: US 11,977,068 B2
(45) Date of Patent: May 7, 2024

(54) METHOD FOR TESTING ECOTOXICITY OF DISINFECTION BY-PRODUCTS

(71) Applicant: Tongji University, Shanghai (CN)

(72) Inventors: Wenhai Chu, Shanghai (CN); Zuxin Xu, Shanghai (CN); Xinmiao Luan, Shanghai (CN)

(73) Assignee: TONGJI UNIVERSITY, Shanghai (CN)

( * ) Notice: Subject to any disclaimer, the term of this patent is extended or adjusted under 35 U.S.C. 154(b) by 607 days.

(21) Appl. No.: 17/148,592

(22) Filed: Jan. 14, 2021

(65) Prior Publication Data
US 2021/0318285 A1    Oct. 14, 2021

(30) Foreign Application Priority Data
Apr. 14, 2020 (CN) .......................... 202010289995.3

(51) Int. Cl.
*G01N 33/18* (2006.01)
*A61K 49/00* (2006.01)

(52) U.S. Cl.
CPC ....... *G01N 33/186* (2013.01); *A61K 49/0008* (2013.01); *G01N 33/18* (2013.01)

(58) Field of Classification Search
CPC ................................................ A61K 49/0008
See application file for complete search history.

(56) References Cited

FOREIGN PATENT DOCUMENTS

| CN | 106719442 A | 5/2017 |
|----|-------------|--------|
| CN | 113661951 * | 11/2021 |

OTHER PUBLICATIONS

Sorgeloos et al., Exotoxicology and Environmental Safety, 1978; 2: 249-255 (Year: 1978).*
CN113661951—google translated (Year: 2021).*
Chun-Hong Ta et al., Chlorination Disinfection by-Products and Their Influencing Factors, Liaoning Chemical Industry, Jan. 2012, pp. 29-31, vol. 41, No. 1.
Chang-Yi Zhou et al., Study on toxicity and safety evalution of triazophos on four species of hydrophytic organisms, Journal of Oceanography in Taiwan Strait, Aug. 2003, pp. 320-324, vol. 22, No. 3.

* cited by examiner

*Primary Examiner* — Brian Gangle
*Assistant Examiner* — Lakia J Jackson-Tongue
(74) *Attorney, Agent, or Firm* — Bayramoglu Law Offices LLC

(57) ABSTRACT

A method for testing ecotoxicity of disinfection by-products (DBPs) is disclosed, including the following steps: firstly, hatching and culturing a brine shrimp to obtain a second-instar brine shrimp larvae; secondly, putting the brine shrimp larvae into a water sample containing the DBPs, obtaining a survival rate through acute toxicity exposure and chronic toxicity exposure, respectively, to calculate the toxicity of the water sample to brine shrimp. The new method includes both acute and chronic toxicity tests. The test water sample can be either a single substance solution or an actual disinfection water sample. The brine shrimp has high sensitivity and is convenient to hatch and culture. The raw materials are inexpensive and easily available. The requirements for the culture environment are not high, and the toxicity end-point is clear. The new method is simple, sensitive and economical, and therefore, a popularization is feasible in sewage and reuse water plants.

8 Claims, 1 Drawing Sheet

METHOD FOR TESTING ECOTOXICITY OF DISINFECTION BY-PRODUCTS

CROSS REFERENCE TO THE RELATED APPLICATIONS

This application is based upon and claims priority to Chinese Patent Application No. 202010289995.3, filed on Apr. 14, 2020, the entire contents of which are incorporated herein by reference.

TECHNICAL FIELD

The present invention relates to the technical field of environmental health and water quality analysis, and in particular, to a method for testing ecotoxicity of disinfection by-products.

BACKGROUND

Climate change, industrial and agricultural development and population growth have collectively led to global water shortage. Reclaimed water, capable of being used in industry, agriculture and other fields, has become an important alternative water resource to meet the growing demand for water resources. Disinfection is generally the last step in wastewater reuse to reduce the pathogenic risk of the reclaimed water. Additionally, chlorine disinfection process is a means to degrade refractory pollutants in some advanced wastewater treatment plants. However, chlorine produces a variety of disinfection by-products (DBPs) when killing pathogenic microorganisms, which presents certain ecological risks to the receiving water body after reclaimed water or sewage reenters the environment.

Since 1974, the health risks of disinfection by-products such as chloroform in drinking water have been widely studied and reported. However, the composition of organic substances in reclaimed water and sewage is quite different from that in drinking water, and the level and types of DBPs generated are also different. The studies showed that the cytotoxicity of sewage could be increased 6 times by disinfection. It is of great significance for municipal construction, environmental protection and public health construction to evaluate the ecological risk of the receiving water body such as a river or ocean after sewage is discharged into the environment.

Brine shrimp (genus *Artemia*) is a typical filter-feeding zooplankton, which is at the bottom of the trophic level and occupies an important position in the marine ecosystem. Additionally, it has a small body size, is sensitivity to pollutants, has salinity tolerance, is inexpensive and is easy to reproduce. Brine shrimp is especially suitable, therefore, as a test organism for toxic effect experiments and is widely used in ecotoxicology research. For many years, most toxicity tests on brine shrimp have been acute toxicity tests, however, it is difficult to simulate the impact of DBPs on the life and survival of organisms after the DBPs enter a water body under actual conditions.

In the prior art, brine shrimp larvae are directly exposed to the toxic chemicals, and the swimming times of the brine shrimp larvae within specified seconds are observed after a short period of time, which makes the test simple and fast. Another method is to use a kit for detection and counting after the brine shrimp are exposed for 24 h, which is fast and accurate. The exposure time of these two methods is too short to detect the effect of DBPs with low content but obvious long-term toxicity to brine shrimp. In addition, the swimming times and the inhibition of swimming speed are used as the end-point of the toxicity test. This places stress on the requirements of the operating equipment and results are not sufficiently clear.

It also consumes substantial manpower, and the experimental results are subjective. The control of brine shrimp instar also affects the results. In the prior art, brine shrimp that has been hatched for 2 days is directly tested. The eggs and larvae of the brine shrimp are typically mixed throughout and, as a result, the instar of the hatched larvae cannot be accurately controlled. The tolerance of brine shrimp in different life stages is different, which leads to the instability of the experimental results. Moreover, brine shrimp in the instar III stage is tested and it is found that its tolerance is high, and DBPs with low content and low toxicity in water are difficult to produce lethal effects on such brine shrimp.

At present, the toxicity tests of disinfected water samples are mainly divided into in vitro experiments and in vivo experiments. In vitro experiments mainly refer to genotoxicity test and cytotoxicity test using a variety of cells, including (1) genotoxicity test: Comet assay, SOS/umu test and Ames test using DNA damage/repair of Chinese hamster ovary cells (CHO cells); (2) cytotoxicity test: cell experiments using CHO cells, human bladder cancer cells, etc. In vivo experiments mainly refer to the lethal or sublethal experiments on model organisms in the unit of bacteria, planktonic or benthic animals, fish or mammals. For in vitro experiments, for example, CHO cell test system commonly used in the toxicity test of disinfection by-products in drinking water has the advantages of high sensitivity and close relationship with human cells. However, cell culture has high requirements on experimental technology and experimental environment, which makes it difficult to popularize it in sewage and reuse water plants. For in vivo experiments, most studies use freshwater organisms as model organisms (for example, *Daphnia magna*), and are susceptible to external factors such as increased salinity caused by concentration of water samples, leading to a reduced credibility of the results.

SUMMARY

In view of the shortcomings and deficiencies of the prior art, a method for testing ecotoxicity of disinfection by-products (DBPs) is provided, including the following steps: S1, hatching anhydrous freeze-dried eggs of a brine shrimp in artificial seawater to obtain a first-instar brine shrimp; S2, culturing the first-instar brine shrimp for 24 h to obtain a second-instar brine shrimp; and S3, exposing the second-instar brine shrimp to a water sample to be tested containing toxic substances for a toxicity test, and after a time end-point of the toxicity test is reached, obtaining a mortality rate of the brine shrimp; wherein, the toxicity test includes an acute toxicity test and a chronic toxicity test; a time end-point of the acute toxicity test is (42-54) h, and a time end-point of the chronic toxicity test is (12-16) days.

Preferably, the artificial seawater is prepared by ultra-pure water and sea salt and filtered by a glass fiber filter membrane with a pore size of 0.22 μm; a salinity of the artificial seawater is 30-40%.

Preferably, a hatching temperature of the first-instar brine shrimp is (24-28)° C. The hatching is performed under a continuous aeration for a hatching time of (10-24) h. An aeration gas source is air. A culture temperature of the first-instar brine shrimp is (24-27)° C., and the culturing is performed in a light incubator for 24 h. A light time and a dark time are respectively continuous 12 h; and a light intensity in the light incubator is (1,000-3,000) Lux.

Preferably, after S1, the first-instar brine shrimp and non-hatched brine shrimp eggs are separated immediately, and the first-instar brine shrimp is placed in the artificial seawater.

Preferably, S3 includes two steps of transferring the second-instar brine shrimp: first, pre-placing the second-instar brine shrimp in the water sample to be tested for a predetermined time, and then putting the second-instar brine shrimp into a culture plate containing the water sample to be tested.

Preferably, the culture plate is a polystyrene cell culture plate with 12 culture wells. The water sample to be tested is a mixed solution of the artificial seawater and the DBPs. The 12 culture wells are divided into several groups containing the water sample to be tested with different concentrations of the DBPs. Each group contains 3-5 culture wells, and each group contains the water sample to be tested with the same concentration of the DBPs. The DBPs includes haloacetic acid, haloacetamide or haloacetonitrile.

Preferably, during the chronic toxicity test, the water sample to be tested is replaced every two days, the brine shrimp is fed, and a feeding density is approximately $1\times10^6$-$10\times10^6$ particles/mL.

Preferably, when the toxicity test reaches the time endpoint, the culture plate is slightly vibrated to observe the survival of the brine shrimp in each well. The judgment basis is that if a larva's appendages on a thoracic segment do not move within 10 s, it is deemed to be dead.

The present invention has the following advantages based on the above technical solution compared with the prior art:

1. The method for testing ecotoxicity of DBPs provided by the present invention combines acute toxicity test with chronic toxicity test, which can not only evaluate the short-term ecological impact brought by DBPs entering the receiving water body, but also simulate the more real environmental conditions of DBPs with low concentration and long-term exposure. Therefore, a comprehensive evaluation on the ecological impact of disinfection is achieved. Compared with similar toxicity tests on freshwater aquatic organisms such as *Daphnia magna*, brine shrimp, as a haloduric marine zooplankton, can avoid the adverse biological effects caused by water sample concentration and salinity increase. Compared with cytotoxicity tests and luminescent bacteria tests on mammals, the method of the present invention has the advantages of low cost and easy technical implementation, which improves the safety of reclaimed water and sewage discharge, thus providing guarantee for ecological protection of water environment.

2. The method for testing ecotoxicity of DBPs provided by the present invention uses brine shrimp as the model organism to avoid the influence of high-salinity environment on the survival of organisms after water sample enrichment. Additionally, the method of the present application has high sensitivity and can be used for testing a variety of disinfection water samples. The brine shrimp can be hatched and cultured with simple operations. The raw materials are inexpensive and easily available. The culture does not require a highly strict environment. The end-point of toxicity test is clear. The method is a simple, sensitive, economical toxicity test method, and therefore, a popularization is feasible in sewage and reuse water plants.

3. The method for testing ecotoxicity of DBPs provided by the present invention can effectively reduce the influence of seawater inevitably existing in the pipette on the concentration of the DBPs in the water sample to be tested through the two steps of transferring the second-instar brine shrimp.

DETAILED DESCRIPTION OF THE EMBODIMENTS

The present invention will be described in more detail below with reference to the figures of the embodiments of the present invention. However, the present invention may be implemented in various forms and should not be interpreted as limited by the embodiments presented herein. On the contrary, these embodiments are proposed to achieve full and complete disclosure, and to make those skilled in the art fully understand the scope of the present invention. In these figures, the size and relative size of layers and regions may be enlarged for clarity.

Figure 1:
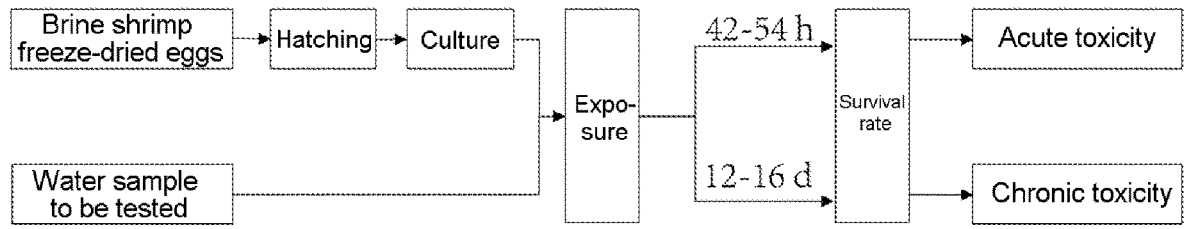
FIG. 1 is a diagram showing a process of the present invention.

As shown in FIG. 1, the present invention provides a method for testing ecotoxicity of DBPs, including the following steps. S1, anhydrous freeze-dried eggs of a brine shrimp are hatched in artificial seawater to obtain a first-instar brine shrimp, where, a hatching temperature is $(26\pm1)°$ C., the hatching is performed under a continuous aeration for a hatching time of (10-24) h, and an aeration gas source is air. After the hatching is finished, the first-instar brine shrimp and non-hatched brine shrimp eggs are separated immediately, and the first-instar brine shrimp is placed in the artificial seawater. The brine shrimp at different life stages may have different tolerance to toxicity, and therefore, a separation of the brine shrimp at different instars can avoid the instability of experimental results. S2, the first-instar brine shrimp is cultured in a light incubator for 24 h to obtain a second-instar brine shrimp, where, a culture temperature is $(26\pm1)°$ C., a light time and a dark time are respectively continuous 12 h, and a light intensity in the light incubator is (1,000-3,000) Lux. S3. First, the second-instar brine shrimp is pre-placed in a water sample to be tested containing toxic substances and exposed for a predetermined time to enable the artificial seawater carried by the second-instar brine shrimp to mix uniformly with the water sample to be tested, and then the second-instar brine shrimp is put into a culture plate containing the water sample to be tested for an acute toxicity test with a time end-point of (42-54) h and a chronic toxicity test with a time end-point of (12-16) days. After the time end-point of the toxicity test is reached, the culture plate is slightly vibrated to observe the survival of the brine shrimp in each well. The judgment basis is that if a larva's appendages on a thoracic segment do not move within 10 s, it is deemed to be dead. A mortality rate of the brine shrimp is obtained to calculate the toxicity of the water sample to the brine shrimp.

It is worth noting that the hatching time, culturing time, environmental temperature and light intensity mentioned in the present application can be adjusted according to the actual water body conditions, and are not limited to the above descriptions.

The artificial seawater is prepared by ultra-pure water and sea salt and filtered by a glass fiber filter membrane with a pore size of 0.22 µm; a salinity of the artificial seawater is $(35\pm1)\%$.

The culture plate is a polystyrene cell culture plate with 6 or 12 culture wells, and the water sample to be tested is a mixed solution of the artificial seawater and the DBPs. The culture wells are divided into several groups containing the water sample to be tested with different concentrations of the DBPs. Each group contains 3-5 culture wells, and each group contains the water sample to be tested with the same concentration of the DBPs. In the actual process, the culture plate with other well number can be used or the group number of different concentrations can be changed to flexibly realize a control experiment. The DBPs in the water sample to be tested are haloacetamide or haloacetic acid, but are not limited to these two kinds of substances.

During the chronic toxicity test, the water sample to be tested is replaced every two days, the brine shrimp is fed with *Chlorella vulgaris* or *Chaetoceros muelleri*, and a feeding density is approximately $1 \times 10^6 - 10 \times 10^6$ particles/mL. The feeding species is not limited to *Chlorella vulgaris* or *Chaetoceros muelleri*, but can also be other algae. The frequency of water exchange can also be adjusted according to the nature and content of the toxic substances in the actual water body.

The following two embodiments are presented for specific illustration.

Embodiment 1

Preparation of artificial seawater: sea salt is added into ultra-pure water to adjust a salinity to $(35\pm1)$‰, filtered through a glass fiber filter membrane with a pore size of 0.22 μm, and poured into a brown bottle for temporary storage, which is ready-to-use.

Preparation of water samples to be tested: a predetermined mass of iodoacetamide (IAM) is weighed and dissolved in the prepared artificial seawater. Four groups of the water samples with different concentrations of IAM are prepared, and each group of the water sample is 500 mL.

Hatching of a brine shrimp: 3-5 g of anhydrous freeze-dried eggs of the brine shrimp is put into a 1,500 mL beaker containing 1,200 mL of seawater. The opening of the beaker is sealed with aluminum foil and the beaker is placed in a constant temperature water bath at $(26\pm1)°$ C. A small air pump is used to blow air for aeration and hatching for 12 h. After the hatching is finished, the first-instar brine shrimp is randomly picked out with a Pasteur pipette immediately and placed in a 150 mm crystallization dish containing sufficient seawater.

Culture of the brine shrimp: the first-instar brine shrimp is cultured in a light incubator for 24 h. The conditions in the light incubator are as follows: a temperature is $(25\pm1)°$ C., a light intensity is 1,000 Lux, and a light time and a dark time are respectively continuous 12 h.

Acute toxicity test: 150 mL of each water sample to be tested is put into a brown bottle, four groups of the water samples with different concentrations of IAM are added into a 12-well culture plate with a pipette, with 2.5 mL of liquid in each well, and each 3 wells is an experimental group with the same concentration of the water samples. The remaining solution in each brown bottle is poured into a clean 150 mm crystallization dish. At least 30 second-instar brine shrimps are transferred into 100-150 mL of the water sample to be tested at one time by the Pasteur pipette in the crystallizing dish, respectively. The second-instar brine shrimps that have been exposed to the solution are transferred by the Pasteur pipette to the culture wells with 10 second-instar brine shrimps in each well. The culture plate is cultured in light. The survival of the brine shrimps in each well is observed after 48 h. The time difference of transferring brine shrimps within and between groups should be shortened as far as possible to avoid the influence of excessive time difference on brine shrimp growth.

Figure 2:
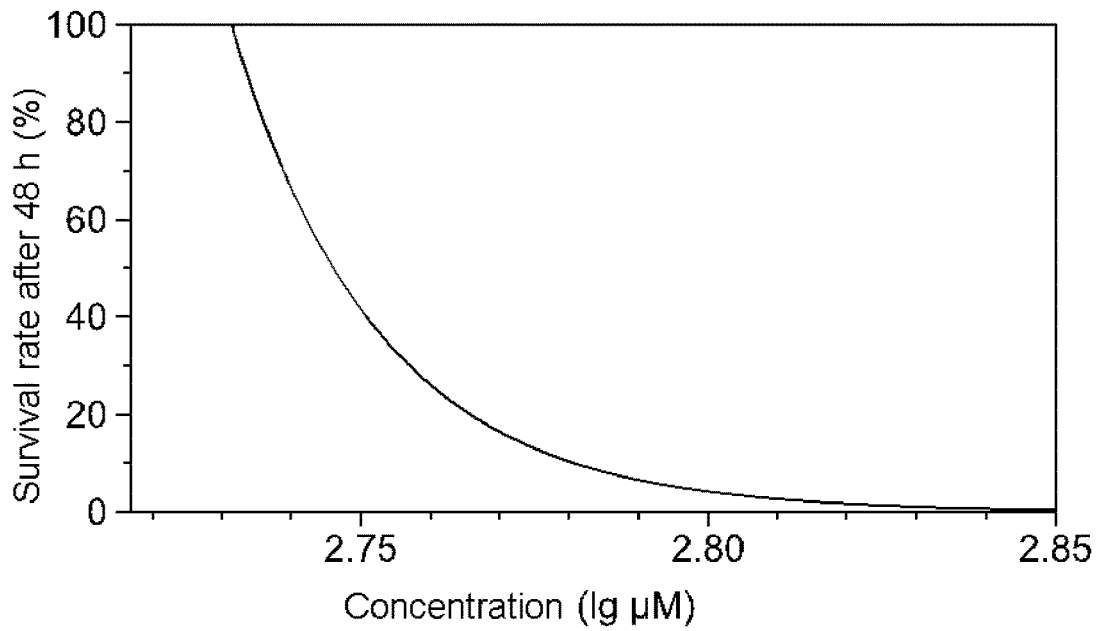
FIG. 2 is a diagram showing data of the embodiment 1 provided by the present invention.

Processing of acute toxicity test data: in embodiment 1, data fitting is performed using SPSS Statistics software, and the following relationship is obtained between brine shrimp survival rate (P, unit is %) and logarithm of IAM concentration (lgC, unit is lg (μM)): $P = \exp(-125 + 354/\lg C)$ $(R^2 = 0.871)$. By calculating the data in FIG. 2, it can be obtained that the median lethal concentration after 48 h (48 h-$LC_{50}$) is 557.262 μM, and the minimum effective concentration (defined as the concentration causing 20% death) is 544.5 μM.

Chronic toxicity test: the chronic toxicity test is carried out under an acute minimum effective concentration (544.5 μM). 150 mL of an IAM water sample with a concentration of 544.5 μM is put into the brown bottle. The water sample to be tested is added into three wells of the 12-well culture plate with the pipette, with 2.5 mL of liquid in each well. The remaining solution in each brown bottle is poured into a clean 150 mm crystallization dish. At least 30 second-instar brine shrimps are transferred into 100-150 mL of water samples to be tested at one time by the Pasteur pipette in the crystallizing dish, respectively. The second-instar brine shrimps which have been exposed to the solution are transferred by the Pasteur pipette to the culture wells with 10 second-instar brine shrimps in each well. The culture plate is cultured in light. The survival of the brine shrimps is observed every 24 h. The IAM solution is exchanged once a day, and the brine shrimps are fed with a sufficient amount of *Chaetoceros muelleri* mixed with *Chlorella vulgaris*. After 14 days, the survival of the brine shrimps in each culture plate is observed and counted. The control group and IAM experimental group should be symmetrically distributed in the six test wells in the center of the culture plate to avoid edge effect. The time difference of transferring brine shrimps within and between groups should be shortened as far as possible to avoid the influence of excessive time difference on brine shrimp growth.

Results: at the concentration of 544.5 μM, the survival rate of brine shrimp is 0. In other words, IAM causes the chronic death of brine shrimp and the mortality rate is 100% under this acute minimum effective concentration. The results show that although this concentration does not cause significant impact on the survival of brine shrimp in a short period of 48 h, a long-term exposure of 14 days will cause a large number of brine shrimp deaths.

Embodiment 2

Preparation of artificial seawater: sea salt is added into ultra-pure water to adjust a salinity to $(35\pm1)$‰, filtered through a glass fiber filter membrane with a pore size of 0.22 μm, and poured into a brown bottle for temporary storage, which is ready-to-use.

Preparation of water samples to be tested: a predetermined mass of iodoacetic acid (IAA) is weighed and dissolved in the prepared artificial seawater. Ten groups of the water samples with different concentrations of IAA are prepared, and each group of the water sample is 500 mL.

Hatching of a brine shrimp: 5 g of anhydrous freeze-dried eggs of the brine shrimp is put into a 1,500 mL beaker containing 1,200 mL of seawater. The opening of the beaker is sealed with aluminum foil and the beaker is placed in a constant temperature water bath at $(27\pm1)°$ C. A small air pump is used to blow air for aeration and hatching for 10 h.

After the hatching is finished, the first-instar brine shrimp is randomly picked out with a Pasteur pipette immediately and placed in a 150 mm crystallization dish containing sufficient seawater.

Culture of the brine shrimp: the first-instar brine shrimp is cultured in a light incubator for 24 h. The conditions in the light incubator are as follows: a temperature is $(25\pm1)°$ C., a light intensity is 1,000 Lux, and a light time and a dark time are respectively continuous 12 h.

Acute toxicity test: 150 mL of each water sample to be tested is put into a brown bottle, ten groups of the water samples with different concentrations of IAA are added into a 12-well culture plate with a pipette, with 2.3 mL of liquid in each well, and each 3 wells is an experimental group with the same concentration of the water samples. The remaining solution in each brown bottle is poured into a clean crystallization dish. At least 30 second-instar brine shrimps are transferred into 100-150 mL of the water sample to be tested at one time by the Pasteur pipette in the crystallizing dish, respectively. The second-instar brine shrimps which have been exposed to the solution are transferred by the Pasteur pipette to the culture wells with 10 second-instar brine shrimps in each well. The culture plate is cultured in light. The survival of the brine shrimps in each well is observed after 54 h. The time difference of transferring brine shrimps within and between groups should be shortened as far as possible to avoid the influence of excessive time difference on brine shrimp growth.

Figure 3:
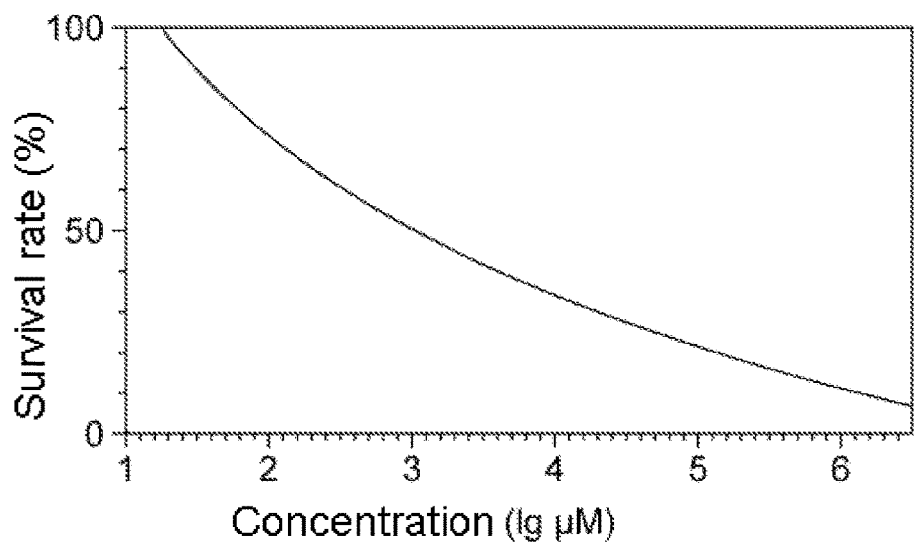
FIG. 3 is a diagram showing data of the embodiment 2 provided by the present invention.

Processing of acute toxicity test data: in embodiment 2, data fitting is performed using SPSS Statistics software, and the following relationship is obtained between brine shrimp survival rate (P, unit is %) and logarithm of IAA concentration (lgC, unit is lg (1 μM)): $P=112.449-56.502 \ln(lgC)$ ($R^2=0.832$). By calculating the data in FIG. 3, it can be obtained that the median lethal concentration after 54 h (54 h-$LC_{50}$) is 1045.201 μM, and the minimum effective concentration (defined as the concentration causing 20% death) is 59.588 μM.

Chronic toxicity test: the chronic toxicity test is carried out under an acute minimum effective concentration (59.588 μM). 150 mL of an IAA water sample with a concentration of 59.6 μM is put into the brown bottle. The water sample to be tested is added into three wells of the 12-well culture plate with the pipette, with 2.3 mL of liquid in each well. The remaining solution in each brown bottle is poured into a clean crystallization dish. At least 30 second-instar brine shrimps are transferred into 100-150 mL of water samples to be tested at one time by the Pasteur pipette in the crystallizing dish, respectively. The second-instar brine shrimps which have been exposed to the solution are transferred by the Pasteur pipette to the culture wells with 10 second-instar brine shrimps in each well. The culture plate is cultured in light. The survival of the brine shrimps is observed every 24 h. The IAA solution is exchanged every two days, and the brine shrimps are fed with a sufficient amount of *Chaetoceros muelleri* mixed with *Chlorella vulgaris*. After 16 days, the survival of the brine shrimps in each culture plate is observed and counted.

Results: at the concentration of 59.588 μM, the survival rate of brine shrimp is 0. In other words, IAA causes the chronic death of brine shrimp and the mortality rate is 100% under this acute minimum effective concentration. The results show that although this concentration does not cause significant impact on the survival of brine shrimp in a short period of 54 h, a long-term exposure of 16 days will cause a large number of brine shrimp deaths.

As it should be understood by those skilled in the art, the present invention may be realized in many other specific forms without departing from its own spirit or scope. Although embodiments of the present invention have been described, it should be understood that the present invention should not be limited to these embodiments, and those skilled in the art may make variations and modifications within the spirit and scope of the present invention as defined in the claims.

What is claimed is:

1. A method for testing an ecotoxicity of disinfection by-products (DBPs), comprising the following steps:
   S1, hatching anhydrous freeze-dried eggs of a brine shrimp in artificial seawater to obtain a first-instar brine shrimp;
   S2, culturing the first-instar brine shrimp to obtain a second-instar brine shrimp; and
   S3, exposing the second-instar brine shrimp to a water sample to be tested for a toxicity test, wherein the water sample to be tested contains toxic substances, and after a time end-point of the toxicity test is reached, obtaining a mortality rate of the second-instar brine shrimp; wherein, the toxicity test comprises an acute toxicity test and a chronic toxicity test; the time end-point of the acute toxicity test is (42-54) h, and the time end-point of the chronic toxicity test is (12-16) days.

2. The method according to claim 1, wherein the artificial seawater is prepared by mixing ultra-pure water and sea salt to obtain a mixture, and filtering the mixture by a glass fiber filter membrane, wherein the glass fiber filter membrane has a pore size of 0.22 μm; wherein a salinity of the artificial seawater is 30-40‰.

3. The method according to claim 1, wherein a hatching temperature of the first-instar brine shrimp is $(24-28)°$ C.; the hatching is performed under a continuous aeration for a hatching time of (10-24) h, and an aeration gas source of the continuous aeration is air;
   a culture temperature of the first-instar brine shrimp is $(24-27)°$ C., the culturing is performed in a light incubator for 24 h, and a light time and a dark time are respectively continuous 12 h; a light intensity in the light incubator is (1,000-3,000) Lux.

4. The method according to claim 1, wherein after S1, the first-instar brine shrimp and non-hatched brine shrimp eggs are separated immediately, and the first-instar brine shrimp is placed in the artificial seawater.

5. The method according to claim 1, wherein S3 comprises two steps of transferring the second-instar brine shrimp: first, pre-placing the second-instar brine shrimp in the water sample to be tested for a predetermined time, and then putting the second-instar brine shrimp into a culture plate, wherein the culture plate contains the water sample to be tested.

6. The method according to claim 1, wherein a culture plate is a polystyrene cell culture plate with 6 or 12 culture wells; the water sample to be tested is a mixed solution of the artificial seawater and the DBPs; the 6 or 12 culture wells are divided into a plurality of groups, the plurality of groups contain the water sample to be tested with different concentrations of the DBPs, each group of the plurality of groups contains 3-5 culture wells, and each group contains the water sample to be tested with a same concentration of the DBPs; the DBPs comprise haloacetic acid, haloacetamide or haloacetonitrile.

7. The method according to claim 1, wherein during the chronic toxicity test, the water sample to be tested is periodically replaced, the second-instar brine shrimp is fed, and a feeding density is approximately $1\times10^6$-$10\times10^6$ particles/mL.

8. The method according to claim 7, wherein when the toxicity test reaches the time end-point, a culture plate is slightly vibrated to observe survival of the second-instar brine shrimp in each well; a judgment basis is that if appendages on a thoracic segment of the second-instar brine shrimp do not move within 10 s, the second-instar brine shrimp is deemed to be dead.

* * * * *